United States Patent
Storz

(10) Patent No.: US 9,272,103 B2
(45) Date of Patent: Mar. 1, 2016

(54) VAPORIZER WITH COMBINED AIR AND RADIATION HEATING

(71) Applicant: Stobi GmbH & Co. KG, Tuttlingen (DE)

(72) Inventor: Markus Storz, Tuttlingen (DE)

(73) Assignee: Stobi GmbH Co. & KG, Tuttlingen (DE)

( * ) Notice: Subject to any disclaimer, the term of this patent is extended or adjusted under 35 U.S.C. 154(b) by 398 days.

(21) Appl. No.: 13/687,545

(22) Filed: Nov. 28, 2012

(65) Prior Publication Data

US 2013/0139813 A1 Jun. 6, 2013

(30) Foreign Application Priority Data

Dec. 1, 2011 (EP) ..................................... 11401648

(51) Int. Cl.
*A61M 15/00* (2006.01)
*A61M 11/00* (2006.01)
*A61M 11/04* (2006.01)

(52) U.S. Cl.
CPC ............ *A61M 15/009* (2013.01); *A61M 11/041* (2013.01); *A61M 11/042* (2014.02); *A61M 15/00* (2013.01); *A61M 2205/3368* (2013.01); *A61M 2205/3653* (2013.01)

(58) Field of Classification Search
CPC . A61M 15/009; A61M 11/041; A61M 15/00; A61M 11/042; A61M 11/04; A61M 11/00; A61M 16/10; A61M 16/16; A61M 16/1075; A61M 16/162; A61M 16/167; A61M 16/1085; A61M 16/109; A61M 16/1095; A61M 11/06; A61M 16/108; A61M 15/06; A61H 33/06; A61H 33/12; A45D 20/08; A45D 20/00; A45D 19/16; A45D 19/00; A45D 20/12; A24F 47/00; A24F 47/008; B05B 17/06; B05B 17/04; B05B 17/0615; F28D 7/10; F28D 7/106

USPC ............ 128/200.14, 200.19, 200.24, 201.25, 128/202.21, 203.12, 203.15, 203.16, 128/203.17, 203.21, 203.22, 203.23, 128/203.24, 203.25, 203.26, 203.27, 128/204.13, 204.17, 204.18, 204.21, 128/205.27, 205.29, 207.14; 392/407, 410, 392/432–434; 96/361–364, 376; 261/DIG. 65; 131/194; 239/128, 239/135–139

See application file for complete search history.

(56) References Cited

U.S. PATENT DOCUMENTS

| | | | | |
|---|---|---|---|---|
| 3,559,886 | A * | 2/1971 | Howard | 239/136 |
| 4,101,611 | A * | 7/1978 | Williams | 261/142 |
| 4,114,022 | A * | 9/1978 | Braulke, III | 392/383 |

(Continued)

FOREIGN PATENT DOCUMENTS

| | | |
|---|---|---|
| DE | 19803376 | 10/1999 |
| DE | 10042396 | 3/2002 |

(Continued)

*Primary Examiner* — Annette Dixon
(74) *Attorney, Agent, or Firm* — Schlee IP International, P.C.; Alexander R. Schlee

(57) ABSTRACT

A hot air extraction vaporizer that is provided with a heat exchanger, a filling chamber for accommodating a substance generating an aerosol when subjected to heat, and a vaporizer outlet for inhaling the aerosol/air mixture. The heat exchanger is in a thermally conductive connection with the filling chamber that when heated up subjects the substance to radiant heat. The heat exchanger is provided with at least one airflow channel generating a hot airflow. The filling chamber comprises at least one of airflow passages and a mesh allowing the hot airflow to pass through the filling chamber and the substance provided therein.

10 Claims, 3 Drawing Sheets

(56) References Cited

U.S. PATENT DOCUMENTS

| | | | |
|---|---|---|---|
| 4,699,136 A * | 10/1987 | Krauser | 128/203.22 |
| 4,955,372 A * | 9/1990 | Blackmer et al. | 128/203.16 |
| 5,031,612 A * | 7/1991 | Clementi | 128/204.14 |
| 6,513,524 B1 | 2/2003 | Storz | |
| 2003/0217750 A1* | 11/2003 | Amirpour et al. | 128/203.25 |
| 2011/0120482 A1* | 5/2011 | Brenneise | 131/328 |
| 2011/0126831 A1* | 6/2011 | Fernandez Pernia | 128/203.27 |

FOREIGN PATENT DOCUMENTS

| | | |
|---|---|---|
| EP | 0858744 | 8/1998 |
| EP | 2210637 | 7/2010 |
| WO | 99/11311 | 3/1999 |

\* cited by examiner

VAPORIZER WITH COMBINED AIR AND RADIATION HEATING

CROSS-REFERENCE TO RELATED APPLICATION

This application claims the priority of the European patent application EP 11401648.8 having a filing date of Dec. 1, 2011. The entire content of this prior European patent application EP 11401648.8 is herewith incorporated by reference.

BACKGROUND OF THE INVENTION

The invention relates to a hot air extraction vaporizer comprising a heater for heating a substance that generates an aerosol when subjected to heat and mixes into an airflow when this airflow flows through the substance, and can either be inhaled via a mouthpiece after being stored in an intermediate storage volume or can be inhaled directly.

Such therapeutic vaporizer apparatuses for generating aroma and/or active ingredient vapors for inhalation are known from the prior art in various styles. For example, the German patents DE 100 42 396 B4 and DE 198 03 376 C1 are mentioned in this connection. These vaporizers provide thermal vaporization and subsequent inhalation of substances that vaporize under heat and form an aerosol.

Simple hot air in extraction vaporizers only have a heated filling chamber for heating the substance to be vaporized via heat radiation. These are inexpensive to manufacture but provide only a somewhat insufficient vaporization since the non-heated air flowing into the filling chamber and seeping through the substance provided therein has a cooling effect and therefore interrupts the vaporization process. This requires then waiting until the radiant heat of the filling chamber has heated up the substance again to the extent that it can be vaporized. Hot air extraction vaporizers that operate only on the basis of radiant heat are at best suitable for pure substances but are operational only to a limited extent when vaporizing aromas or active ingredients from medicinal herbs.

More efficient is a method where the substance is subjected to a hot airflow that is heated by passing a heat generator. The hot air seeps through the filling chamber holding the substance, wherein the substance vaporizes and its active ingredients, for instance medicinal herbs, are vaporized (extracted) from a substrate and then mixed into the hot air. This hot air may carry for instance all aromas and/or active ingredients is then inhaled as breathing in air after it has been cooled down to a temperature that is comfortable for inhaling, allowing the active ingredients to be absorbed by the lung into the blood circulation. For the purpose of the hot air extraction typically medicinal herbs or other suitable plant substances are used that are shredded to the size that is useful for the purpose of application or possibly also synthetic substances and therapeutic substances that may be provided in form of a powder. It is also possible to vaporize liquid substances. For forming an aerosol, the substances need to be subjected for example to a temperature of for example 390° F. by the hot air. Typical evaporation temperatures range between approximately 250 to 500° F., specifically between 266 and 446° F. (130-230° C.).

For a more effective method for heating air typically a heat exchanger is used that comprises at least one air channel for the air flow that is to be heated up. The air channel may run internally through the heat exchanger or may encompass the heat exchanger from the outside. There are also implementations where electrical heating wires are provided in an open fashion within the air channel. In general, prior art hot air extraction vaporizers implement two basic principles for generating a hot airflow via a heat exchanger. According to one embodiment, the airflow may be generated by sucking out air at an outlet opening or in another alternative embodiment by blowing in air from an inlet opening of the air channel, generating the required high or low pressure either by a person's lung or by using a blower or pump, for instance a membrane pump. By the thermal contact with the heat generator the air from the environment flowing through an inlet of the vaporizer is heated up by the heat exchanger from ambient temperature to for instance 390° F. (199° C.) depending on a temperature and a volume flow through the air channel. The temperature is matched with the boiling or extraction temperature for inhalation of the substance forming the aerosol so that the active ingredients and/or aromas are vaporized by the hot airflow seeping through the filling chamber and the aerosol is carried by the airflow. After passing through the filling chamber with the substance generating the aerosol the airflow carrying the aerosol is provided for breathing in or for inhaling.

However, first of all, the hot airflow as well as the cold substances and the cold filling chamber need to be heated up so that vaporization of these substances is generally possible.

By using hot air extraction vaporizers comprising a pump and an intermediate storage such as for instance a plastic inhalation bag as described in the German patent DE 19803376 C1 the disadvantages are limited since the non-enriched pure air provided for inhalation is mixed with air that has been enriched by the aromas and/or active ingredients before the mixture is inhaled from the intermediate storage. However, applying the present invention to this type of hot air extraction vaporizers including a pump and an intermediate storage would also result in a more effective vaporization.

In contrast, when using hot air extraction vaporizers using a hot airflow that is directly inhaled from the inhaler or sucked in therefrom the problem occurs that at first several breaths are required for heating up the cold substances as well as the surrounding cold filling chamber with the hot airflow since prior to heating up no vaporization can happen. Apart from this process bothering the user, the user is also not aware when exactly vaporization starts.

It is an object of the invention to improve the prior art to the extent that for hot air extraction vaporizers where inhalation is performed straight out of the vaporizer already with the first breathing in and thereafter continuously aroma vapors and active ingredient vapors are provided.

BRIEF SUMMARY OF THE INVENTION

This is achieved according to the invention by a hot air extraction vaporizer, comprising: a heat exchanger; a filling chamber for accommodating a substance generating an aerosol when subjected to heat; and a vaporizer outlet for inhaling the aerosol/air mixture; wherein the heat exchanger is in an thermally conductive connection with the filling chamber that when heated up subjects the substance to radiant heat; the heat exchanger comprises at least one airflow channel generating a hot airflow; and the filling chamber comprises at least one of airflow passages and a mesh allowing the hot airflow to pass through the filling chamber and the substance provided therein.

This is further achieved by a method of generating an aerosol by extracting a volatile substance from a substance substrate and mixing it with air, the method comprising opening a filling chamber, inserting the substrate, heating the filling chamber to a temperature between 250° F. and 500° F.

thus subjecting the substrate to radiant heat, generating a hot air stream and guiding the hot air stream through the filling chamber and passing the hot air stream through the substrate thus generating the aerosol, cooling the aerosol to a temperature that feels comfortable for inhaling, and guiding the cooled aerosol to an outlet with a mouthpiece for inhaling.

DETAILED DESCRIPTION OF THE INVENTION

It is the idea of the invention that heating in a hot air extraction vaporizer can be enhanced such that an immediate vaporization takes place that also continues throughout the inhalation process.

Accordingly, the hot air extraction vaporizer according to the invention comprises a heater that is capable of heating the filling chamber as well as capable of generating a hot airflow that is guided through the content of the filling chamber. For this purpose, the heater, which may be designed as a solid heat exchanger and comprise one or more air channels running through the heat exchanger, may preferably according to one embodiment comprise a filling chamber that is integrated into the heat exchanger; and according to another preferred embodiment a detachable filling chamber, that is in the attached state thermally coupled via a contact face with the heat exchanger. The inner wall of the filling chamber is in both cases designed to heat up the content of the filling chamber via radiant heat. The heated inner wall of the filling chamber heats the content via heat radiation and at the side via thermal contact of the content with the wall of the filling chamber irrespective of hot airflow passing through the filling chamber. Heating the filling chamber is sufficient for heating up the aerosol generating substances to a temperature for generating an aerosol and to maintain this temperature even when the filling chamber is not penetrated by air. If the filling chamber is subjected to an airflow flowing therethrough, it has first been heated up, so that the content of the filling chamber is not cooled but its temperature is maintained at a level required for forming the aerosol and this temperature is maintained jointly with the filling chamber.

Although the invention is directed to hot air extraction vaporizers for direct inhalation by the user, the invention is not restricted to such hot air extraction vaporizers but is in general directed to the hot air extraction vaporizer as mentioned at the outset. The invention is for example also advantageous for hot air extraction vaporizers having an intermediate storage into which the aerosol/air mixture is first pumped and then later inhaled from the intermediate storage.

Preferably, the filling chamber comprises an inner heat conductive component part that is for instance made from metal, and forms specifically the inner wall of the filling chamber or an inner chamber housing and an outer, thermally well insulating and circumferentially encompassing component part that can be made for instance from plastic. In an embodiment where the heat exchanger comprises an integrated filling chamber the inner chamber housing is part of the heat exchanger.

In a design comprising the detachable filling chamber the heat conductive inner chamber housing can for instance abut with its front face against the heat exchanger. This allows during the heating process or also when the heat exchanger has already been heated up a fast heat transfer from the heat exchanger to the chamber housing via direct heat conduction. In this case, the inner chamber housing encompassing the filling chamber holding the substances to be vaporized and bordering the filling chamber is made from a highly heat conductive material such as for example metal.

In the heat exchanger having an integrated or an abutting inner chamber housing moist substances accommodated in the filling chamber such as plant material dries still during the heating up phase before the inhalation is started. The water of the plant material evaporates within a short time span, typically in less than 1 minute. After drying the plant material or more generally drying any substances generating aerosol under heat and being provided in the filling chamber, the aerosol generating substance can be released from the plant material by forces exerted by the lung generating the hot airflow and can be inhaled with the breathe in air. As long as the substance contains moisture this prevents heating beyond the boiling point of water. Moisture prevents keeping the substance to the temperature that is required for generating aerosol.

According to a preferred embodiment of the invention the inner chamber housing is cylindrical and accommodated within the vaporizer housing in an axially movable fashion. This is in particular advantageous when the heat exchanger likewise has a substantially cylindrical cross section. This allows to position the inner chamber housing with the filling chamber in a simple fashion on the front face of and coaxially with the air channel at the heat exchanger such that the airflow exiting the heat exchanger can be guided through air passages that are provided in a bottom and a cap of the filling chamber holding the substances that are provided for the hot air extraction. The bottom and/or the cap of the filling chamber may in the alternative be made from a metal wire mesh.

According to a preferred embodiment of the hot air extraction vaporizer according to the invention a detachable filling chamber is provided that comprises at its outer circumference a thread engaging its counterpart thread provided on the vaporizer housing. The thread may be provided at an inner circumference or an outer circumference of the filling chamber wherein the counter thread of the vaporizer housing is designed in a complementing fashion and disposed for engagement. Twisting the filling chamber in relation to the vaporizer housing of the hot air extraction vaporizer generates in twisting direction a solid connection by the generated forces and seals the chamber housing against the heat exchanger. The same applies for the filling chamber cap that may be provided independently from the integrated and detachable filling chamber and in the same aforementioned fashion connected with the filling chamber.

In addition, the outer chamber housing comprises according to a preferred embodiment of the invention a thermally insulated release lever for twisting the chamber housing or the filling chamber in relation to the vaporizer housing. This saves the user from suffering burns when detaching or attaching the filling chamber to the heated up heat exchanger.

According to a preferred embodiment of the hot air extraction vaporizer according to the invention the vaporizer is designed as a hand-held apparatus comprising a handle. For this purpose, a part of the vaporizer housing encompassing the heat exchanger can be designed as a handle or in the alternative the vaporizer housing comprises a handle that is provided at a side thereof.

The invention is explained in the following in more detail by referring to the embodiment shown in the drawings. Additional features of the invention can be gathered from the following description of an embodiment of the invention in combination with the claims and the attached drawings. The individual features may be implemented by itself or in combination for various embodiments of the invention.

DETAILED DESCRIPTION OF THE DRAWINGS

Figure 1:
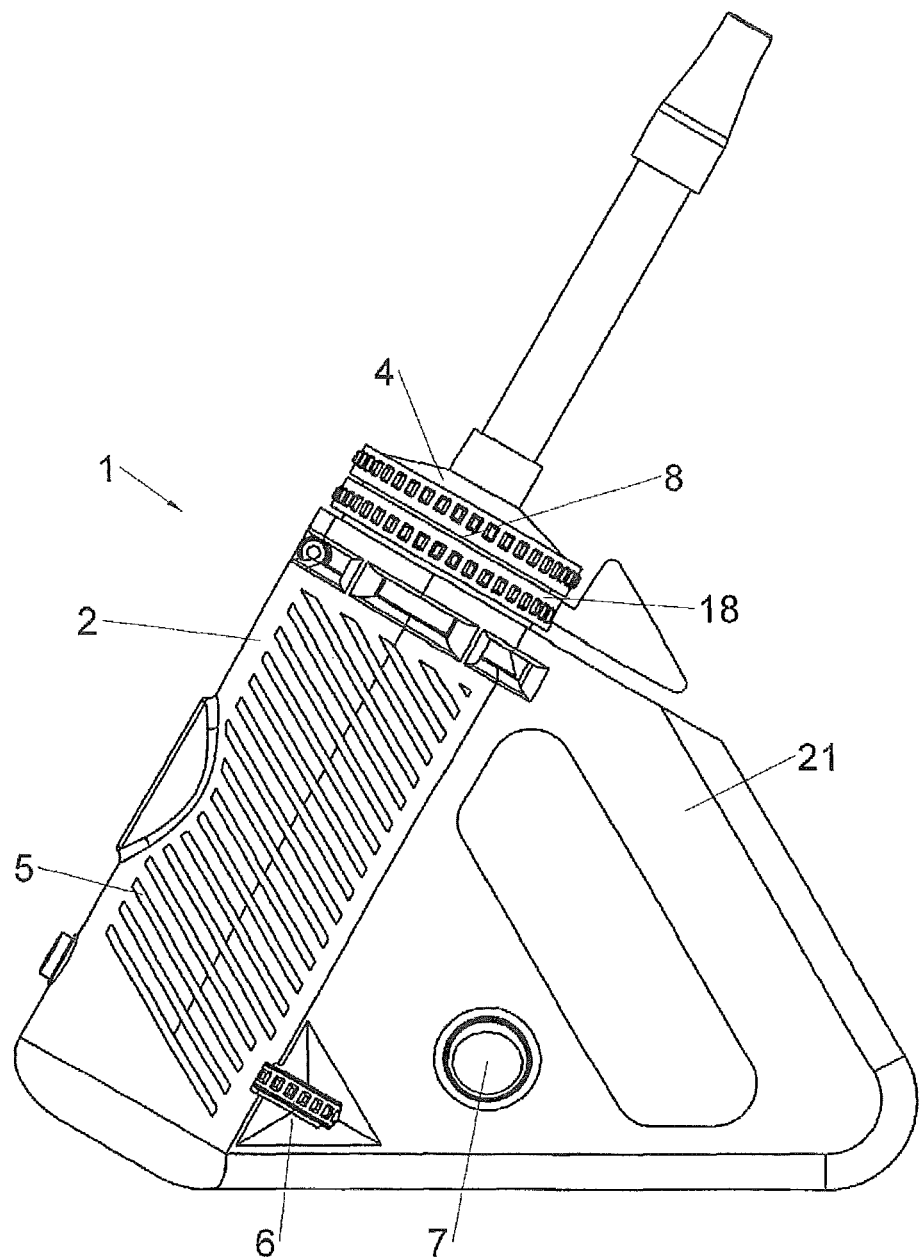
FIG. 1 is a side view of a hot air extraction vaporizer with a detachable filling chamber according to the present invention.

FIG. 1 shows an embodiment of the hot air extraction vaporizer 1 according to the invention, comprising a vaporizer housing 2 accommodating a heat insulated heat exchanger 3 (FIG. 2) for heating an airflow. When the vaporizer outlet 4 of the hot air extraction vaporizer 1 is subjected to a low pressure or vacuum, for instance by inhaling air from the hot air extraction vaporizer 1 through the vaporizer outlet 4, air flows through the ventilation slots 5 into the vaporizer housing 2 and enters subsequently from there into the heat exchanger 3. After having passed through the heat exchanger 3 and the detachable filling chamber 8 the air exits at the vaporizer outlet 4. The heat exchanger 3 is heated electrically, the temperature can be set by a temperature selector 6, and supply voltage can be switched on and off via the mains voltage switch 7.

Figure 2:
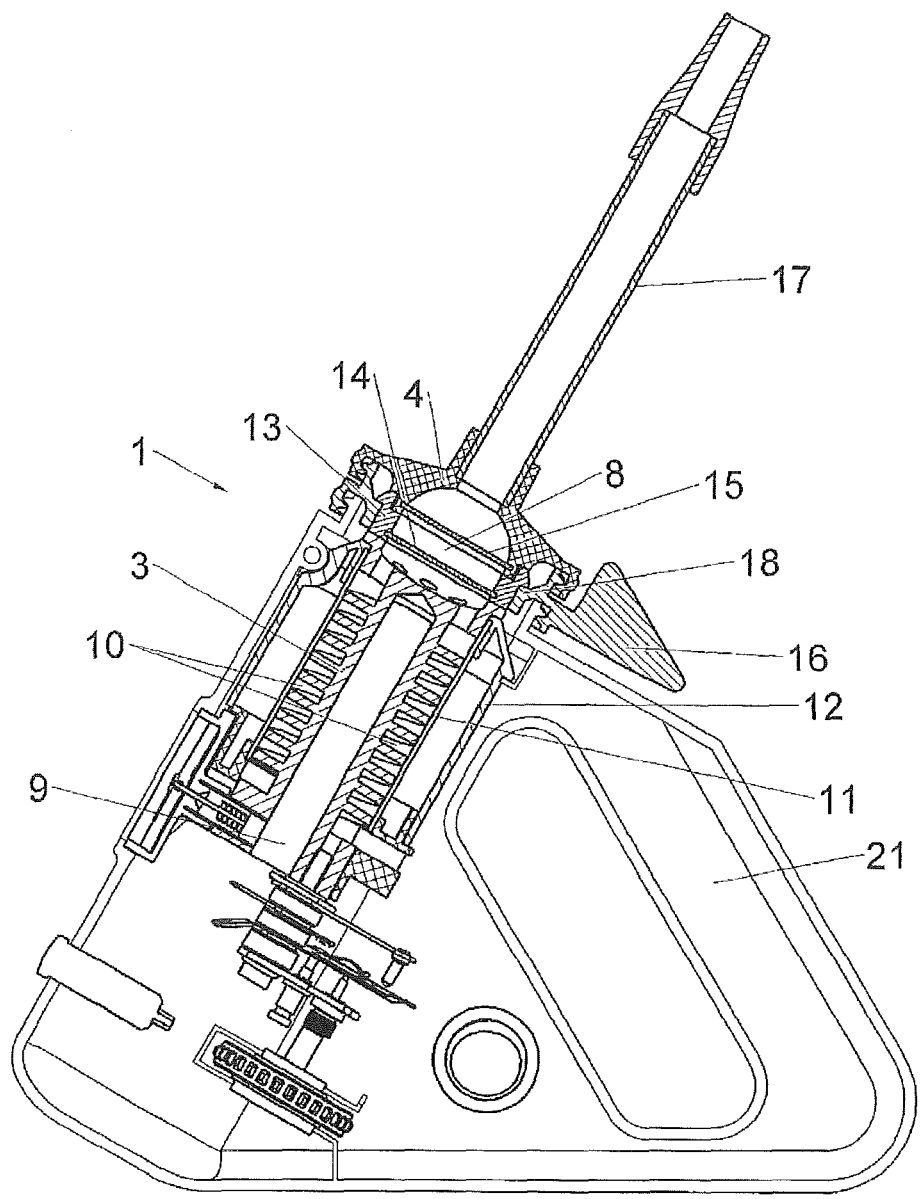
FIG. 2 is a sectional view of the hot air extraction vaporizer according to FIG. 1.

FIG. 2 shows a sectional view of the interior of the vaporizer housing 2. Shown are the vaporizer housing 2 and the heat exchanger 3 as well as the filling chamber 8 for accommodating substances that generate an aerosol when subjected to heat, wherein the filling chamber 8 is provided in the direction of flow as an extension of the heat exchanger 3 between that heat exchanger 3 and the vaporizer outlet 4. The heat exchanger 3 comprises a centrally located heating cartridge 9 as well as two helical air channels 10 that are sealed at their outer circumference by the outer tube 11. The outer tube 11 is encompassed by an insulating sheath 12 for thermally insulating the heat exchanger 3 with respect to the vaporizer housing 2. The heating cartridge 9 and the heat exchanger 3 form in connection with the outer tube 11 a heater of the hot air extraction vaporizer 1.

The filling chamber 8 comprises an inner chamber housing 13 with a chamber bottom 14 and comprises the vaporizer outlet 4 and the chamber cap 15, wherein the vaporizer outlet 4 is detachable from the outer chamber housing 18 for filling or emptying the filling chamber 8. The filling chamber 8 is provided coaxially with respect to the heat exchanger 3 and is movable in axial direction within the vaporizer housing 2. The filling chamber 8 is detachable by a thermally insulated release lever 16. The vaporizer outlet is dome-shaped and comprises heat insulation properties. The vaporizer outlet 4 carries the chamber cap 15 that is designed like the chamber bottom 14 to be air permeable, for instance perforated, and is attached to a suction hose 17 that protrudes from the vaporizer housing 2 and allows for breathing in (inhaling) air coming from the hot air extraction vaporizer 1.

Figure 3:
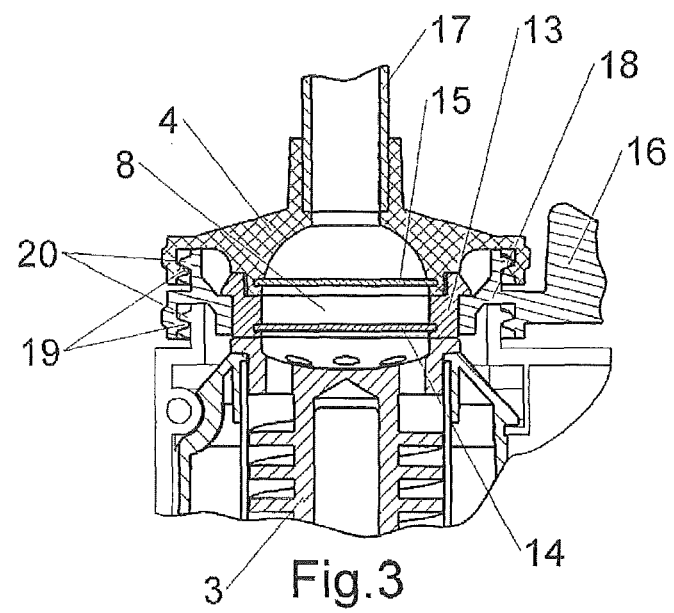
FIG. 3 is an enlarged detail sectional view of the vaporizer outlet shown in FIG. 2.

FIG. 3 shows an enlarged sectional view of that end of the heat exchanger 3 that faces the vaporizer outlet 4 as well as the filling chamber 8 provided downstream of the heat exchanger 3 and the subsequent vaporizer outlet 4. In comparison to FIG. 2, this shows in more detail the filling chamber 8 with the internal chamber housing 13, the outer chamber housing 18, the chamber bottom 14 and the chamber cap 15.

The filling chamber 8 can be opened by removing the vaporizer outlet 4 together with the suction hose 17 and the chamber cap 15 from the inner and outer chamber housings 13 and 18. FIG. 3 shows the inner chamber housing 13 with its front face abutting against the heat exchanger 3 so that a direct thermal contact is provided between the heated heat exchanger 3 and the inner chamber housing 13, allowing the inner chamber housing 13 to be heated by heat conduction and therefore heating the substance (not shown in the drawings) generating aerosol that is provided within the filling chamber 8 by heat radiation emanating from the inner chamber housing 13.

According to this preferred embodiment, the filling chamber 8 can be removed for convenient emptying, cleaning and refilling from the heat exchanger 3 in axial direction. For this purpose, the chamber housing 13 can be twisted by the radially protruding release lever 16, that engages with the outer chamber housing 18, in relation to the heat exchanger 3 and the vaporizer housing 2 in a circumferential direction of the filling chamber 8. The inner chamber housing 13 is connected to the outer chamber housing 18 by positive interlocking or frictional forces, wherein the release lever 16 is integrally formed with the outer chamber housing 18 and therefore co-rotates therewith. The outer chamber housing 18 that encloses the inner chamber housing 13 comprises a thread 19 and the outer circumference facing the vaporizer housing 2, in this shown embodiment formed by helical wings. The helical wings 19 engage the internal thread 20 of the vaporizer housing 2. Depending on a direction of moving the release lever 16 either clockwise or counterclockwise the filling chamber 8 moves towards the heat exchanger 3 or away therefrom.

Figure 4:
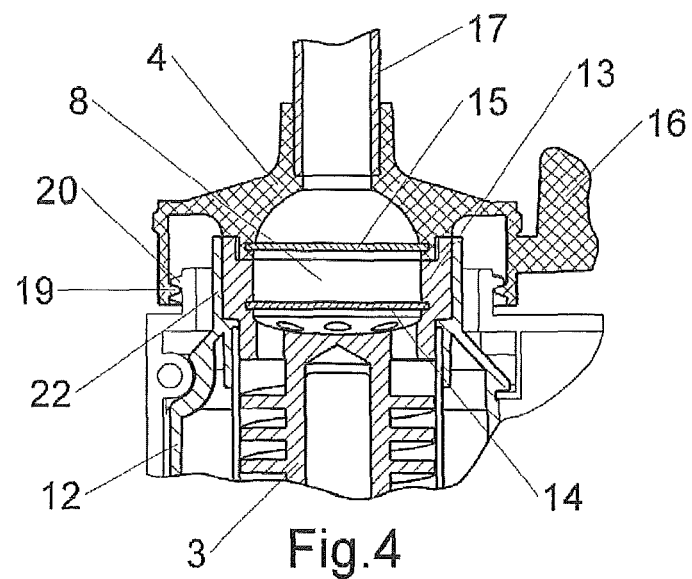
FIG. 4 is an enlarged detail sectional view of the vaporizer outlet comprising an integrated filling chamber.

FIG. 4 also shows a detail of that end of the heat exchanger 3 that faces the vaporizer outlet 4 as well as the downstream filling chamber 8 and the further downstream vaporizer outlet 4. In contrast to FIG. 3, FIG. 4 shows an inner chamber housing 13 of the filling chamber 8, the inner chamber housing 13 being integrated into the heat exchanger 3. The heat exchanger 3 and the inner chamber housing 13 form a joint, integrally formed component part. The outer chamber housing 18 can therefore be omitted in the embodiment shown in FIG. 4 and is substituted by a protecting cylinder 22 that is integrally formed with the insulating sheath 12. The release lever 16 is in this case integrally formed with the vaporizer outlet 4.

The filling chamber 8 can be opened by removing the vaporizer outlet 4 together with the suction hose 17 and the chamber 15 from the inner chamber housing 13. FIG. 4 shows the inner chamber housing 13 as integrally formed with the heat exchanger 3, creating a direct thermal connection between the heated heat exchanger 3 and the inlet chamber housing 13, so that the inner chamber housing 13 is heated by heat conduction and consequently heating a substance, in the drawing not shown, that is capable of generating aerosol and is provided in the filling chamber 8 by heat radiation that emanates from the inner chamber housing 13 and in part also directly from the heat exchanger 3.

The vaporizer outlet 4 according to this embodiment can be removed in axial direction from the filling chamber 8. For this purpose, the vaporizer outlet 4 is twisted by the radially protruding release lever 16 that is connected to the vaporizer outlet 4 with respect to the heat exchanger 3 and the vaporizer housing 2 in a circumferential direction of the filling chamber 8 with the release lever engaging the vaporizer outlet 4. The vaporizer outlet 4 co-rotates with the release lever 16. The vaporizer outlet 4 comprises at its outer circumference facing the vaporizer housing 2 a thread 19 that is designed in the shown embodiment as helical wings. The helical wings 19 engage the related internal thread 20 of the vaporizer housing 2. Depending on the turning direction of the release lever 16 either in clockwise or counterclockwise direction the filling chamber 8 moves towards or away from the heat exchanger 3.

The hot air extraction vaporizer 1 shown in FIGS. 1 through 4 is preferably designed as a tabletop apparatus or as a hand-held apparatus. If designed as a hand-held apparatus, the vaporizer housing 2 is provided with a handle 21 that is provided on one side of the vaporizer housing 2.

What is claimed is:

1. A hot air extraction vaporizer, comprising:
a heat exchanger;
a filling chamber for accommodating a substance generating an aerosol when subjected to heat; and
a vaporizer outlet for inhaling the aerosol/air mixture; wherein
the heat exchanger is in a thermally conductive connection with the filling chamber that when heated up subjects the substance to radiant heat and the same heat exchanger comprises at least one airflow channel generating a hot airflow;
the filling chamber comprises at least one of airflow passages and a mesh allowing the hot airflow to pass through the filling chamber and the substance provided therein;
the filling chamber further comprises an inner chamber housing and is removable together with the inner chamber housing from the heat exchanger, wherein the inner chamber housing is connected in an attached position to the heat exchanger in a heat conductive fashion; and
the inner chamber housing of the filling chamber abuts in its attached position with its front face against the heat exchanger.

2. The hot air extraction vaporizer according to claim 1, wherein the filling chamber further comprises an inner chamber housing that is integrally formed with the heat exchanger.

3. The hot air extraction vaporizer according to claim 1, wherein the filling chamber is cylindrical and is guided within a vaporizer housing in an axially movable fashion.

4. The hot air extraction vaporizer according to claim 1, wherein the filling chamber comprises at its outer circumference a thread that engages a thread of a vaporizer housing.

5. The hot air extraction vaporizer according to claim 1, wherein the filling chamber comprises a thermally insulated release lever for twisting the filling chamber with respect to the vaporizer housing and the heat exchanger.

6. The hot air extraction vaporizer according to claim 1, wherein the vaporizer outlet is attached to the inner chamber housing in a removable fashion.

7. The hot air extraction vaporizer according to claim 1, wherein the hot air extraction vaporizer is designed as a hand-held apparatus with a handle provided at a vaporizer housing.

8. A method of generating an aerosol by extracting a volatile substance from a substance substrate and mixing it with air, the method comprising:
opening a filling chamber;
inserting the substrate;
attaching the filling chamber to the heat exchanger so that an inner chamber housing of the filling chamber abuts in its attached position with its front face against the heat exchanger in a heat conductive fashion;
heating the filling chamber to a temperature between 250° F. and 500° F. thus subjecting the substrate to radiant heat;
generating a hot air stream and guiding the hot air stream through the filling chamber and passing the hot air stream through the substrate thus generating the aerosol;
cooling the aerosol to a temperature that feels comfortable for inhaling; and
guiding the cooled aerosol to an outlet with a mouthpiece for inhaling.

9. The method according to claim 8, further comprising generating the hot airflow by a user generating with his lungs a pressure below ambient pressure at the mouthpiece sucking air through a heat exchanger channel passing from there through the filling chamber to the mouthpiece.

10. The method according to claim 8, further comprising generating the hot airflow by a pump generating a pressure above ambient pressure and passing this pressurized air through a heat exchanger channel passing from there through the filling chamber to the mouthpiece.

* * * * *